United States Patent [19]

Schilling

[11] Patent Number: 5,059,399
[45] Date of Patent: Oct. 22, 1991

[54] CRYOGENIC SELF-SEEDING VIAL

[76] Inventor: Dean W. Schilling, 400 Hoover Rd., Soquel, Calif. 95073

[21] Appl. No.: 455,266

[22] Filed: Dec. 22, 1989

[51] Int. Cl.$^5$ ............................................... B01L 3/14
[52] U.S. Cl. ................................... 422/102; 220/408; 220/410
[58] Field of Search ................. 422/102; 220/446, 447, 220/408, 410; 215/354

[56] References Cited

U.S. PATENT DOCUMENTS

| 3,272,579 | 9/1966 | Leonard | 220/446 |
| 4,338,814 | 6/1983 | Schilling | 73/118.2 |
| 4,390,111 | 6/1983 | Robbins et al. | 215/354 |
| 4,915,255 | 4/1990 | Curtis | 220/408 |

Primary Examiner—Robert J. Warden
Assistant Examiner—Laura E. Collins
Attorney, Agent, or Firm—James R. Haller; Gregory P. Kaihoi; Mary P. Bauman

[57] ABSTRACT

A vial for holding a biological specimen during a cryogenic freezing procedure. The vial includes a wall of a material having a predetermined coefficient of thermal conductivity $K_1$ defining a specimen-receiving internal cavity, and a pin extending in to close proximity with the internal cavity from outside the container. The pin has a coefficient of thermal conductivity $K_2$ substantially greater than $K_1$, and defines a path of increased thermal conductivity from the interior to the exterior of the container to cool a specimen carried therewithin. The container includes an upper open end including a sealing cap, and the pin desirably extends sealingly through the container wall at the bottom end portion of the container.

11 Claims, 5 Drawing Sheets

CRYOGENIC SELF-SEEDING VIAL

FIELD OF THE INVENTION

The invention relates to the field of cold-temperature processing and storage of materials and particularly to the preservation of biological specimens.

BACKGROUND OF THE INVENTION

Biological materials such as semen are commonly preserved by freezing at cryogenic temperatures. The containers which are used for the biological specimens must provide a completely closed and sealed environment to prevent leakage of gases and liquids into the container at cryogenic temperatures. Specimen containers may, for example, be plastic or glass ampoules. The specimen-containing ampoules are cooled below freezing and eventually are transferred to permanent ultra-low temperature storage facilities.

The rate of cooling of a biological specimen during the freezing process may be critical to the ability of the specimen to display viability when eventually thawed. Freezing procedures in the past have employed a method in which plastic or glass specimen containers simply are suspended in a cold vapor for a predetermined period of time to allow the specimens to freeze, and the containers then are plunged into a liquid cryogen such as liquid nitrogen. This relatively simple procedure does not take into account aspects of initiation of ice nucleation ("seeding"), nor is compensation made for the supercooling phenomenon. The phenomenon of supercooling involves the ability of a liquid to be cooled well below its normal freezing point before undergoing a phase change. When freezing occurs, the temperature of the specimen may rapidly increase to approximately the normal freezing point upon liberation of the heat of fusion, following which the temperature of the solid frozen specimen decreases. For example, if a standard 320 milliosmol solution contained in a sealed plastic container were to be permitted to supercool below its normal freezing point as its temperature was gradually lowered, freezing may occur at a temperature of from about $-14°$ to about $-18°$ Celsius. At the moment of the phase change, the sample temperature may dramatically rise toward $-0.5$ to $-1°$ C., before falling again. The resulting fluctuation of temperatures in the vicinity of the freezing point may be very harmful to many biological specimens, and desirably should be avoided as much as possible. Temperature fluctuations have a tendency to harm such biological specimens because it causes alternate cell hydration and cell dehydration through cell wall osmosis. The corresponding water movement weakens the cell wall and diminishes the integrity of the specimen. Accordingly, it is desired to minimize temperature fluctuations due to supercooling to in turn decrease the damage which is done to the sample due to the freezing process.

SUMMARY OF THE INVENTION

The present invention relates to a sealable specimen vial for holding a biological specimen during a freezing procedure and which reduces the magnitude of temperature fluctuations at or near the freezing point of the specimens. The vial comprises a container having a wall of material having a predetermined coefficient of thermal conductivity $K_1$ and defining a specimen-receiving internal cavity. A pin is provided in the wall outside the container to within specimen-cooling proximity with the container cavity, the pin having a coefficient of thermal conductivity $K_2$ that is substantially greater than $K_1$. The pin forms a thermal bridge, that is, a preferred path for heat conductance, from the interior to the exterior of the cavity to transfer heat from and hence cool a specimen carried in the cavity. When the vial is supported in a cryogenic vapor or other cryogenic environment, heat is lost from the vial preferentially through the thermal bridge provided by the pin such that a liquid specimen within the cavity is preferentially cooled at the location of the pin and the pin thus serves to induce local ice nucleation of the specimen. The value of $K_2$ is preferably at least five times greater than $K_1$.

In a preferred embodiment, the container has an upper open end and a lower end portion, and includes a cap for sealing the upper open end. The cap may include shaping means extending therefrom for reception in the container and oriented so that when the cap is sealed to the upper end of the container, the shaping means extends within the container cavity in liquid-displacing contact with a liquid specimen to thereby increase the area of contact of the specimen with the container wall and reduce thickness of the specimen in at least one dimension, to improve heat transfer from the specimen to the vial wall.

DESCRIPTION OF THE PREFERRED EMBODIMENTS

Figure 1:
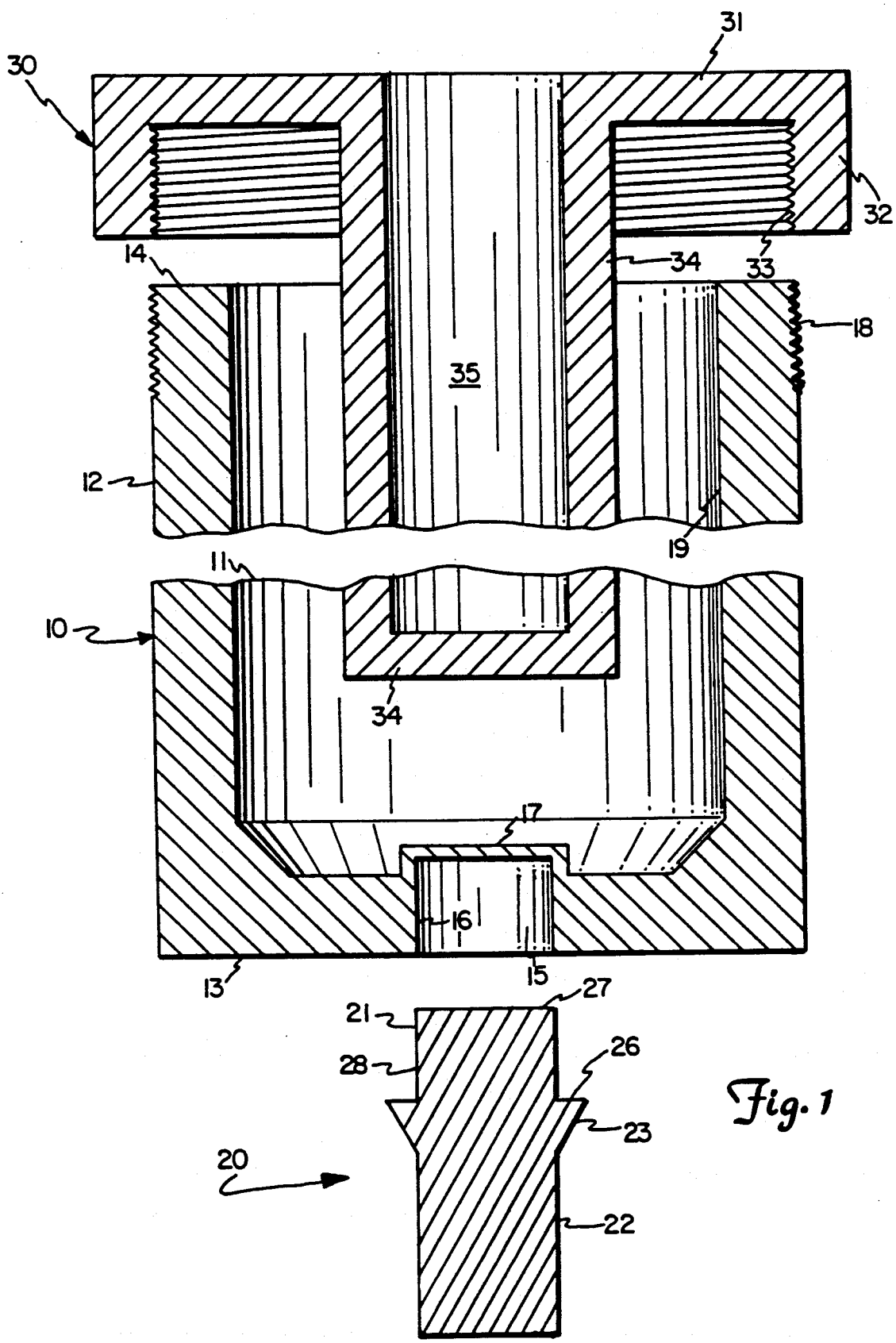
FIG. 1 is a cross-sectional view of a cryogenic self-seeding vial according to this invention.

The present invention provides a vial for cooling samples to cryogenic temperatures which decreases the deleterious effects of supercooling. Referring to FIG. 1, the vial includes a wall (10) with a thermal conductivity of $K_1$ which defines a specimen-receiving internal cavity (11). The cavity may be shaped as desired. The wall preferably comprises a vertical, cylindrical portion (12) integrally formed with a lower end portion (13), which may be substantially perpendicular to the cylindrical portion as shown, or may take any desired shape, such as a generally hemispherical shape providing a wall with a curved portion comprising its lower end.

A sample vial according to the invention also includes a pin (20) with a coefficient of thermal conductivity $K_2$ which includes a head (21) and a shank (22) disposed behind the head. The pin preferably also includes an outwardly extending shoulder (23) disposed between the head and the shank and having a surface (26) abutting the wall (10) when the vial is assembled. The pin desirably has a generally circular cross section, but may take any desired form. The shank (22) may be substantially solid (as in FIG. 1), or may include a plurality of heat transfer fins or flanges as typified at (24) in FIGS. 2 and 3) to improve heat exchange with the surrounding environment.

The wall (10) has at least one pin retention recess (15) formed therein for receiving the head of a pin (20), and this recess may be placed at any location on the wall. In a preferred embodiment, however, one recess is located in the lower end portion (13) and includes an inner surface (16), which may be cylindrical and a protective, thin web (17) of web material extending across the recess, the web being substantially thinner than the wall. The web may extend into the cavity (11) as shown in FIG. 1, thereby increasing the surface area of the upper surface in contact with a specimen retained in the vial. The pin retention recess (15) should be very close to the shape and dimensions of the head (21) of the pin so that the end (27) of the head, disposed away from the shank (22), may engage the web (17) of the recess. The recess is desirably as deep as the length of the head of the pin, allowing the shoulder (23) of the pin to abut an area of the wall adjacent the recess without preventing the head from closely contacting the upper surface of the recess.

Figure 2:
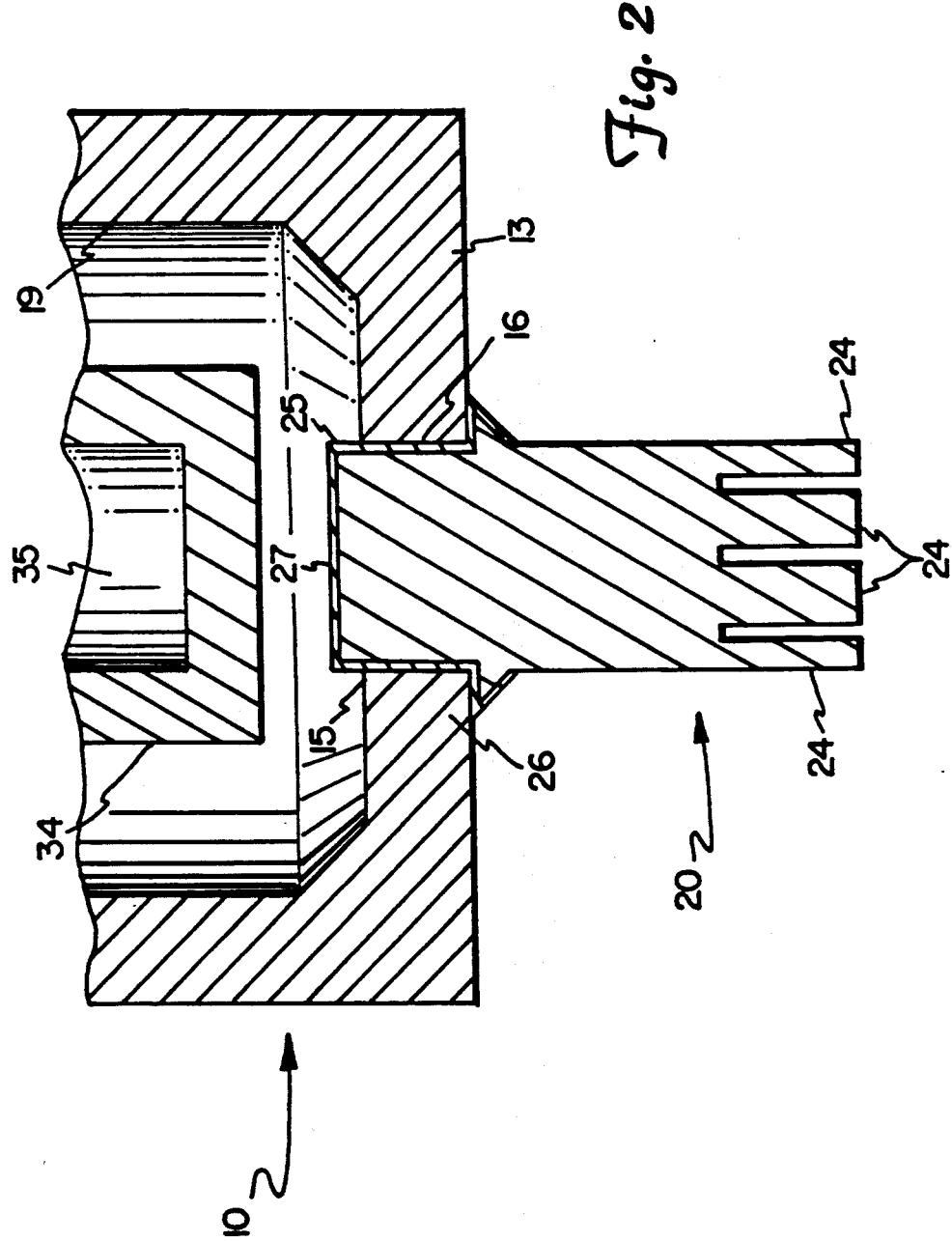
FIG. 2 is a broken away, cross-sectional view of another embodiment of the present invention.
Figure 3:
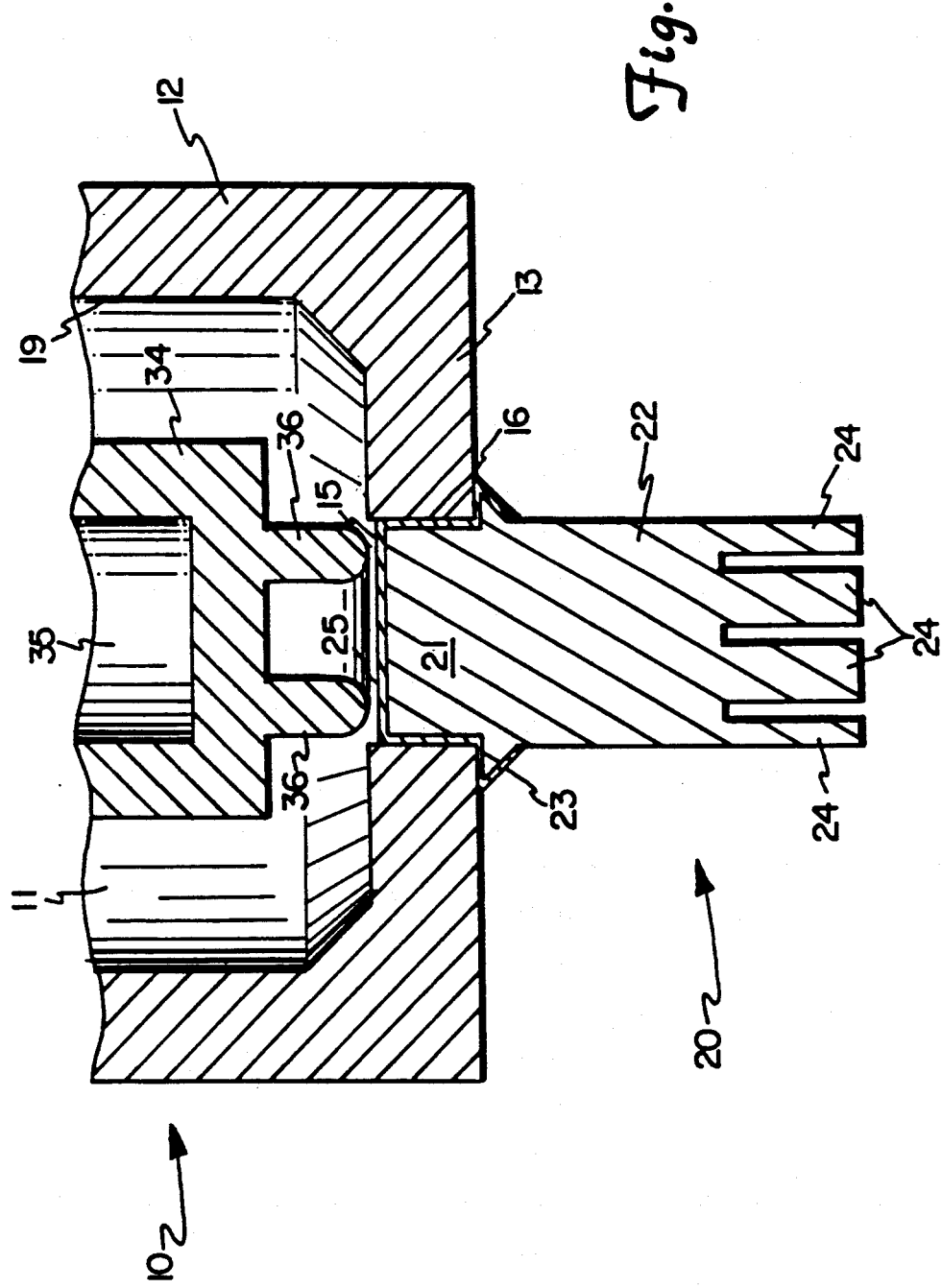
FIG. 3 is a broken-away, cross-sectional view of yet another embodiment of this invention.

In another embodiment, shown in FIG. 2, the pin retention recess (15) extends entirely through the wall (10). The shape and dimensions of the inner surface (16) should closely match those of the head of the pin to ensure close engagement with the pin. The pin's head is desirably of a length greater than the thickness of the wall so that a portion of the pin protrudes into the internal cavity off the vessel, as shown in FIG. 2, but the head of the pin may be shorter so that the pin does not enter the cavity (as shown in FIG. 3). Since such a construction will place the pin in contact with the contents of the vessel, it may be useful to coat the pin with a biologically inert material such as platinum or a plastic material such as polyethylene to prevent contamination of the sample. This pin coating (25) should cover at least that portion of the pin that would otherwise contact the specimen within the vial, and desirably extends from the end (27) of the head rearwardly at least as far as the distal end of the shoulder. The pin coating may cover the entire outer surface of the pin, but it is preferred that a substantial portion of the shank (22), and particularly any heat transfer flanges (24) which may be incorporated in the shank, be left uncovered to provide intimate contact with the cryogenic environment surrounding the vial.

The head (21) of the pin may have a substantially smooth outer surface (28) as shown in FIGS. 1-3, or may be provided with any of a variety of surface irregularities which enhance retention of the pin in the pin retention recess (15). For instance, the surface head (28) may be provided with threads which mate with threads provided on the inner face (16) of the recess. Alternatively, the head may include one or more annular flanges, or barbs or other protrusions which may either press tightly against the surface (16) of the recess or be received by mating irregularities in the surface (16). As an example, an annular flange may be formed about the periphery of the head between the shoulder (23) and the end (27), and positioned to engage an annular groove formed in the surface (16). The flange or the wall of the vial or both may be made of a slightly elastic material which deforms to allow the flange to pass through the recess until the flange engages the groove. If flanges or other protrusions, rather than mating threads, are disposed on the surface of the head, the pin may simply be press fitted into the recess.

Figure 4A:
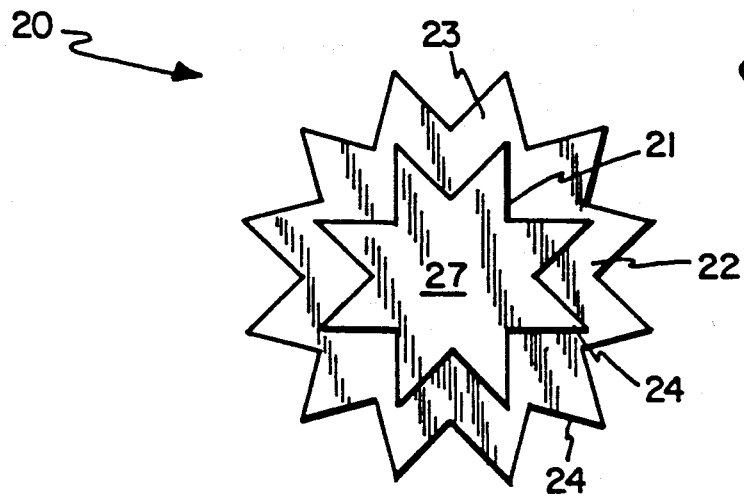
FIGS. 4A and B show a top view and a side view, respectively, of an alternative embodiment of a pin of the invention.
Figure 4B:
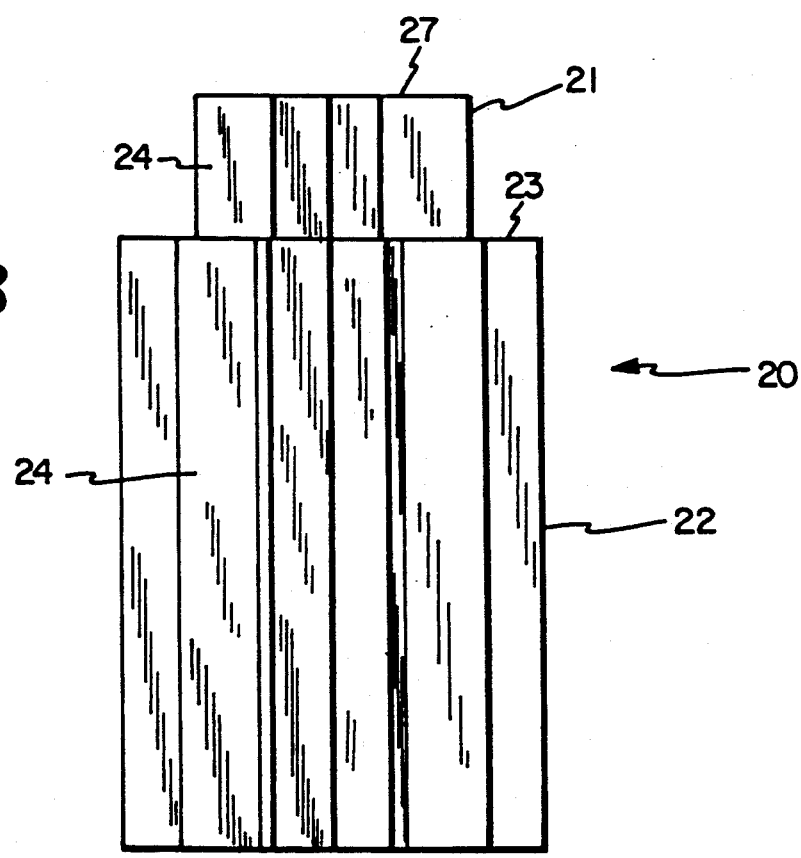

FIGS. 4A and B show another embodiment of a pin of the invention. Both the head (21) and the shank (22) of the pin are provided with a plurality of radially extending heat transfer flanges (24). The pin retention recess (15) of the wall may be formed to mate with the flanges provided on the head and be held in contact with substantially the entire surface thereof. This arrangement aids in retaining the pin in the desired position and, due to the increased surface available for heat transfer, increases the rate of heat transfer from the wall to the pin to allow the contents of the vial to cool more rapidly. The heat transfer flanges (24) on the shank (22) improve heat dissipation from the pin into the cryogenic environment, ensuring that the pin cools significantly more rapidly than the wall of the vial.

A vial according to a preferred embodiment of the present invention also includes a cap (30) which is employed to seal an upper open end (14) of the wall (10). This allows one to place a specimen into the interior cavity (11) through a readily accessible opening and then close the vial to prevent leakage of gas or liquid employed in the freezing process into the container. The cap includes a top member (31) and a side member (32). The top member is desirably large enough to cover the open end (14) of the container and the side member may extend downwardly about the exterior of the cylindrical portion (12) of the wall and be in close contact therewith. If so desired, the cap may instead be designed such that the side member contacts the inner surface of the cylindrical portion and is contained in the upper region of the internal cavity; the primary design consideration is simply that the cap and the wall must meet to form an effective seal. Regardless of which side of the cylindrical portion the side member contacts, this seal may be accomplished by providing threads (33) on the surface of the side member adjacent the wall and similarly including mating threads (18) on the portion of the wall adjacent the side member. Alternatively, a press fit seal may be used. This design may be preferred where the mating thread design would not provide an effective seal, as where the open end (14) is not circular.

The cap (30) may also include a central shaping member (34) which depends from the top member (31) and is received in the internal cavity (11) of the vial. The central member will most commonly be utilized in connection with liquid specimens such as seminal fluid. The specimen is placed in the internal cavity and, as the cap is put in place, the central member (34) descends into the cavity, decreasing the available volume inside the cavity and displacing the liquid. The central member is preferably configured to be uniformly spaced from the inner surface of the wall (19), e.g., if a cylindrical wall is employed, the central member should be cylindrical as well. This increases the surface area of the vial in contact with the specimen, which promotes a quicker, more uniform cooling of the sample material. To further promote these ends, the central member (34) may be spaced only slightly away from the wall, thereby yielding a thin, more easily cooled layer of specimen between the inner wall of the vial and the confronting surface of the central member.

The central member may be solid, but a hollow construction which includes a central void (35) is preferable. The vapors and/or liquid used to cool the specimen may enter the central void to allow the specimen to be cooled more quickly. Moreover, the central void may be shaped to retain the pin (20) for easy storage and more economical packaging and transport; this design also permits containers to be "nested" in the cooling chamber with the pin of one vial held in the central void of another, increasing the capacity of the cooling system. If so desired, the central member or another portion of the cap may include a pin retention recess (15), allowing the pin to be placed into specimen-cooling proximity with the internal cavity (11) through the cap rather than, or in addition to, retaining a pin in the wall (10) of the container.

In a particularly preferred embodiment, the bottom end of the central member, i.e., the end disposed away from the top member (31), is held more closely to the pin (20) (in the vial of FIGS. 2 and 3) or the upper surface (17) of the pin retaining recess (in the vial of FIG. 1) than to the cylindrical portion (12) of the wall. This decreases the volume of the sample adjacent the pin which, as will be explained below, helps minimize the degree of supercooling of a sample and its attendant harmful effects. To further minimize the sample volume near the pin, the central member may be provided with a finger or fingers (36) which extend downwardly from the bottom of the central member toward the pin, as shown in FIG. 3. These fingers serve to minimize the volume of the specimen held between the pin and the central member as well as increasing the cooling rate of the sample in this area by increasing the surface area of the central member.

As mentioned above, the wall (10) has a coefficient of thermal conductivity $K_1$ and the pin (20) has a coefficient of thermal conductivity $K_2$. $K_2$ should be substantially greater than $K_1$ so that the pin cools significantly more quickly than the wall; the ratio $K_2/K_1$ is desirably at least 5 and may be much greater. Materials now commonly utilized for forming containers for samples which are to be cryogenically frozen are glass, polyethylene, polycarbonate, and other similar plastics. Although the thermal conductivity of plastic materials ma vary significantly depending on numerous factors such as molecular weight and degree of crystallinity, glass commonly has thermal conductivity values between about 0.3 and 1.0 Btu-ft/hr-ft$^2$-° F. Although the pin may be formed of a plastic or like material if its K value ($K_2$) is greater than the K value of the wall ($K_1$) as mentioned above, the pin is most desirably made of metal. The thermal conductivity of metals varies greatly, but the metals preferred for use in the invention are stainless steel, aluminum and copper, which have K values of 22-26, about 117, and 207-224 Btu-ft/hr-ft$^2$-° F., respectively.

It was explained above that it may be useful to coat the pin with a biologically inert material, such as a plastic, if the pin is to contact the sample contained in the vial. Although this will obviously tend to decrease the thermal conductivity of the pin, it will not adversely affect the utility of a vial according to the invention if the overall coefficient of thermal conductivity of the pin is sufficiently greater than that of the wall. In this embodiment, if a metal with a high thermal conductivity, such as aluminum, is used and the pin coating (25) is kept relatively thin, the net thermal conductivity of the pin may meet or exceed the aforementioned preferred $K_2/K_1$ ratio of 5. Alternatively, a biologically inert metal, such as platinum, may be used to coat the pin. Since the thermal conductivity of such materials tends to be much greater than that of plastics, this would alleviate the necessity to closely monitor the thickness of the pin coating to ensure a proper $K_2/K_1$ ratio. For reasons explained below, it is also desirable to keep the web (17) of the pin retention recess (15) thin to ensure that the combined thermal conductivity of the pin and the web maintains the desired ratio with that of the wall.

Supercooling of a biological sample being cooled to cryogenic temperatures can damage the sample by breaking down the cell walls, as already noted. Supercooling tends to occur most often when a sample is cooled too quickly for a phase change, such as from liquid to solid, to proceed at equilibrium, as is often the case with cryogenic freezing due to economic and time constraints. This phenomenon may be eliminated, or at least greatly reduced, by providing seed crystals or other nucleation sites which induce crystal growth in the rest of the material. Accordingly, the present invention to induces growth of seed crystals by cooling a portion of the sample adjacent the pin more quickly than the sample as a whole, causing this part of the sample to begin freezing sooner than the rest, providing nucleation sites which propagate crystal formation throughout the material. Although this may cause more damage due to supercooling in areas very near the pin interface, by promoting freezing throughout the sample the net result is a superior frozen material.

This "seeding" is accomplished by forming a thermal bridge, i.e. a preferred path of heat transfer between the interior of the vessel and the cryogenic environment. By providing a pin with a coefficient of thermal conductivity $K_2$ substantially greater than $K_1$, the pin cools significantly cooler than the wall, causing heat to be lost more quickly by the material nearest the interface with the pin. This preferential cooling causes the temperature adjacent the pin to drop more rapidly than in the rest of the sample, thereby reaching a temperature where the phase change may occur sooner than the sample as a whole. Once freezing occurs in this small area, ice crystallization propagates throughout the sample. This localized heat loss and subsequent seeding is enhanced if the cap (30) includes a central member (34) which is spaced closer to the pin than the cylindrical portion (12) of the wall by minimizing the portion of the sample near the pin. The cooling differential between the sample as a whole and this thin cross section of material between the pin and the central member is heightened because a smaller proportion of the sample is immediately affected by the thermal bridge. This not only causes ice nucleation adjacent the pin to occur more quickly, but also decreases the amount of material which is damaged by supercooling.

Figure 5:
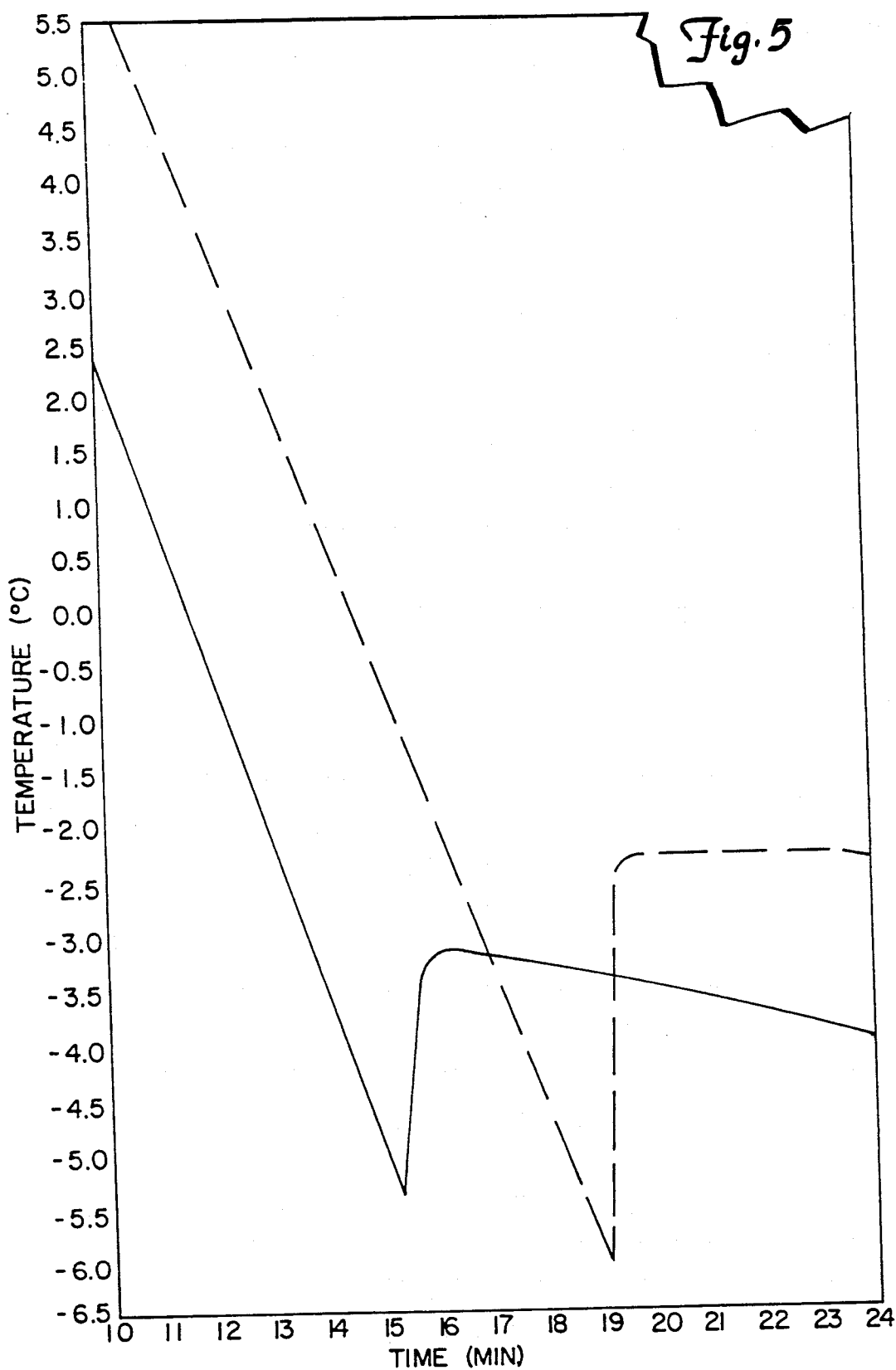
FIG. 5 is a graph of the cooling path of a sample contained in a prior art vial and of a sample contained in a vial according to the present invention.

A sample of semen was placed in a vial according to the invention and a similar sample was placed in a prior art vessel and both samples were frozen by placing them in vapor above a cryogenic liquid. The rate of cooling was controlled by varying the vertical spacing between the vials and the liquid cryogen level as described in U.S Pat. No. 4,388,814, issued to the inventor of the present invention. Both samples were started at room temperature and the ambient temperature adjacent the vials was decreased at a rate of about 1.5° C. per minute down to −16° C. (which took about 17.3 minutes) and were then held at that temperature for 3.3 minutes before being cooled at a rate of 1.2° C. per minute down to −40° C. The samples were subsequently cooled to the temperature of the liquid cryogen and placed therein FIG. 5 is a graph of the temperature of the vials versus time showing the results of this procedure wherein the solid line represents the temperature of the sample in the vial of the invention and the broken line represents the temperature of the sample in the prior art vial.

Both of the time/temperature curves show a jump in temperature which indicates that supercooling took place before the phase changed from liquid to solid. This transition occurred approximately 15.5 minutes after the cooling began for the sample in the vial of the invention while the phase transformation occurred in the prior art container about 19 minutes into the cooling process. Thus, not only did the semen in the new apparatus cool more quickly, as indicated by the steeper slope, but the phase change occurred sooner. More importantly the temperature change at the point of freezing was much lower with the invention than with the prior art device. In the vial according to the invention, the sample's phase change was accompanied by a temperature increase of 1.55° C., from 5.37° C. to 3.82° C.; the material in the old vessel underwent a jump in temperature from −6.1° C. to −2.5° C., or 3.6° C. Hence, the invention decreased the variation in temperature associated with freezing by almost 60% over the prior art.

The significance of this marked improvement in minimizing the effects of supercooling was made clear by testing the semen samples frozen in the two vials. The motility of the semen used was measured before freezing and was found to be 71%, i.e., 71% of the spermatozoa were motile. The semen was mixed with 10% glycerol (v/v) and a sample was placed in a vial of the invention and a prior art vial. The samples were frozen as outlined above, then thawed out and two motility tests were performed on each sample. The first test was performed immediately after thawing while the sample was allowed to sit at room temperature for one hour prior to the second test. The motility was determined by assessing the motility of 100 sperm from each of four areas of a slide containing a portion of the sample under a light microscope. For the prior art container, the motility measured on the first run was 36.8% and the second run yielded a 21.2% motility., this represents a decrease of 48% on the first run from the initial 71% motility of the semen, while the second run showed a 70% drop. The sample in the vial of the invention fared much better. The motility on the first run was found to be 50% (a decrease of 30%) while 34.2% of the spermatozoa were found to be motile in the second run (a decrease of 51.8%). Thus, almost half of the initially motile spermatozoa were destroyed by being frozen in the old container, while more than two-thirds of those in the new vial survived the process. Even after sitting at room temperature for an hour, the sample placed in the invention showed that almost half still remained motile, i e., about the same result obtained without any waiting before testing the sample in the prior art device.

Thus, by providing a pin with a coefficient of thermal conductivity substantially greater than that of the wall, the temperature change upon freezing was decreased by almost 60%. This resulted in much less damage to the sample, as measured by a net increase in motility, in a vial of the invention than in a prior art vessel which did not utilize a thermal bridge.

While a preferred embodiment of the present invention has been described, it should be understood that various changes, adaptations and modifications ma be made therein without departing from the spirit cf the invention and the scope of the appended claims.

What is claimed is:

1. Vial for holding a biological specimen during a cryogenic freezing procedure, comprising a container having a wall of material having a predetermined coefficient of thermal conductivity $K_1$ and defining a specimen-receiving internal cavity, and at least one pin extending into close proximity with the internal cavity from outside the container and having a coefficient of thermal conductivity $K_2$ substantially greater than $K_1$ and defining a path of increased thermal conductivity from the interior to the exterior of the container to cool a specimen carried therein.

2. The vial of claim 1 wherein the ratio $K_2/K_1$ is at least about 5.

3. The vial of claim 1 wherein the container has a lower end portion and an upper open end, the vial including a cap for sealing the upper open end of the container.

4. The vial of claim 3 wherein the pin extends sealingly through the container wall at the bottom end portion of the container.

5. The vial of claim 4 wherein at least a portion of the pin includes a coating of a biologically inert material.

6. The vial of claim 3 wherein the pin extends sealingly through the cap.

7. The vial of claim 6 wherein at least a portion of the pin includes a coating of a biologically inert material.

8. The vial of claim 1 including shaping means extending within the cavity for contacting and displacing a liquid specimen in the cavity to increase the area of contact of the specimen with the container wall.

9. The vial of claim 3 wherein the cap includes shaping means extending therefrom and oriented such that when the cap seals the upper open end of the container the shaping means is received in the container cavity in liquid-displacing contact with a liquid specimen to increase the area of contact between the specimen and the container wall.

10. The vial of claim 9 wherein the pin extends generally vertically downwardly through the container wall at the lower end portion of the container.

11. The vial of claim 9 wherein the cap and the container adjacent its upper open end are provided with cooperating threads to permit the cap to be screwed onto the container.

* * * * *